United States Patent [19]

Wynne et al.

[11] 4,304,719
[45] Dec. 8, 1981

[54] CONDUCTING IODINE-DOPED FLUOROMETALLOPHTHALOCYANINES

[75] Inventors: Kenneth J. Wynne, Falls Church, Va.; Paul Kuznesof, Decatur, Ga.; Ronald Nohr, Springfield, Va.; Malcolm Kenney, Cleveland Heights, Ohio

[73] Assignee: The United States of America as represented by the Secretary of the Navy, Washington, D.C.

[21] Appl. No.: 228,013

[22] Filed: Jan. 23, 1981

[51] Int. Cl.$^3$ .............................................. C09B 47/04
[52] U.S. Cl. ................................. 260/314.5; 521/124; 528/9; 528/362; 252/501.1; 252/518
[58] Field of Search ..................................... 260/314.5

[56] References Cited

U.S. PATENT DOCUMENTS 4,209,458  1/1980  Keller et al. ................... 260/465 F

OTHER PUBLICATIONS

Linsky, Dissertation Abst. International Section B, 31, 3242jB (1970).
Paul, Dissertation Abst. International Section B, 32, 4471B (1972).
Schramm et al., Science, 200, pp. 47–48 (1978).
Petersen et al., J. Am. Chem. Soc., vol. 99, pp. 286–288 (1977).
Orr et al., J. Am. Chem. Soc., vol. 101, pp. 2875–2877 (1979).
Schoch et al., J. Am. Chem. Soc., vol. 101, 7071–7073 (1979).

Primary Examiner—John D. Randolph
Attorney, Agent, or Firm—R. S. Sciascia; A. L. Branning; T. E. McDonnell

[57] ABSTRACT

An iodine-doped polyfluorometallophthalocyanine having the repeating unit of $[(PcMF)(I)_x]$ wherein Pc represents a phthalocyanine moiety, M represents a III-A metal selected from the class consisting of aluminum and gallium, and x is from about 0.01 to about 3.4 if M is aluminum and x is from about 0.01 to about 2.3 if M is gallium.

6 Claims, No Drawings

CONDUCTING IODINE-DOPED FLUOROMETALLOPHTHALOCYANINES

BACKGROUND OF THE INVENTION

Conducting and photoconducting organic and inorganic polymers are becoming increasingly important for optical, electronic, photoelectric and electrochemical applications. Polymers often offer substantial improvements in processability, cost, and properties, both physical and chemical. One property which both polymers and nonpolymers lack to a degree which prevents their use in many important applications is thermal stability. The maximum operational temperature for some conducting and photoconducting polymers and crystals is about 125° C. but for most the maximum temperature is well below 100° C.

Formation of thin films is important in opto-electronic applications because the deposition of thin films on a substrate alters the opto-electronic properties, e.g., photosensitivity, light transmission, electron transmission, and photovoltaic efficiency. Processing thin films is greatly improved if the material sublimes, thereby permitting vacuum deposition of the film.

The opto-electronic properties and thermal stability of phthalocyanine polymers and dyes indicate that these materials would be useful in optical and electronic applications if their extremely low electrical conductivity could be increased. Iodination of some phthalocyanines greatly increases the conductivity of these materials. Excellent conductivity for a single crystal of nickel phthalocyanine iodide ($NiPcI_{1.0}$) has been reported in C. J. Schramm et al., *Science* 200, 47-8 (1978). Conductivities of pressed pellets of metallophthalocyanine iodides ($MPcI_x$) wherein M is Fe, Co, Ni, Cu, Zn, or Pt, are reported in J. L. Petersen et al., *J. Amer. Chem. Soc.*, 99, 286-8 (1977). Upon iodine incorporation the electrical conductivity of films of nickel phthalocyanine is reported to be substantially increased in W. A. Orr and S. C. Dahlberg, *J. Amer. Chem. Soc.*, 101, 2875-7 (1979).

The solid-state properties and utilizibility of these metallomacrocycles depend, to a large degree, on the kind and degree of stacking that occurs with these macrocycles. K. F. Schoch, et al., *J. Amer. Chem. Soc.*, 101, 7071-3 (1979) studied metallophthalocyanine moieties covalently linked to a "face-to-face" orientation by oxygen. The resulting polymer $(MPcO)_n$ wherein M is silicon, germanium, or tin was iodinated to increase the conductivity. Although the conductivity of $[(MPcO)(I)_x]_n$ is much higher than $(MPcO)_n$, the best conductivity reported is only 0.2 ohm $^{-1}$cm$^{-1}$.

Stacked fluorinated polyphthalocyanines represented by the formula: $(PcMF)_n$ have been reported in (1) J. P. Linsky *Dissertation Abstract International Section B*, 31 (1970) 3242B and (2) T. R. Paul *Dissertation Abstract International Section B*, 32 (1972) 4471B. The materials have extremely low conductivities and no successful modification, e.g., iodination has been reported.

Fluorinated polyphthalocyanine condensation resins have been reported in U.S. Pat. No. 4,209,458, issued on June 24, 1980 to Keller et al. These resins, while posessing exceptional structural strength, had very low conductivities.

SUMMARY OF THE INVENTION

It is, therefore, an object of the present invention to synthesize high-temperature conducting and photoconducting polymers.

A further object of the present invention is to synthesize conducting and photoconducting polymers which are suitable for vapor-deposition-fabrication processes.

Another object of the present invention is to provide conducting and photoconducting polymers which are easily and inexpensively synthesized and whose starting materials are readily available.

A further object of the present invention is to synthesize polymers which have a conductivity in excess of 1 ohm $^{-1}$cm$^{-1}$.

A still further object of the present invention is to provide conducting and photoconducting polymers whose use temperatures are in excess of 125° C.

These and other objects are achieved by an iodine-oxidized fluorine-bridged, stacked metal-coordinated polyphthalocyanine prepared by reacting a fluorine-bridged, metal (III-A) coordinated polyphthalocyanine with iodine.

DETAILED DESCRIPTION OF THE INVENTION

The polymers of the present invention are represented by the following formula: $[(PcMF)(I)_x]_n$ wherein Pc represents a phthalocyanine moiety, M is a III-A metal selected from the class consisting of aluminum and gallium, x is from about 0.01 to about 3.4 for aluminum and is from about 0.01 to about 2.3 for gallium and n is the number of repeating units. Because of the fluorine bridged structured formed in the solid state, the polymer has no easily measurable number of repeat units, i.e., it is commonly referred to as having an "infinitely long" chain length. A more detailed formula for the subject polyphthalocyanines is given as follows:

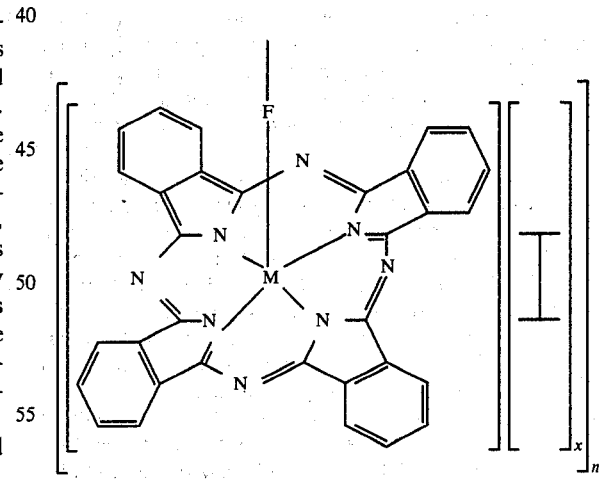

Of particular importance in the polymer are the establishment of an electronic conduction band, the amount of separation between phthalocyanine rings, and the coordinate covalent bridge bonds of the fluorine atoms. The conduction band resulting from oxidation by iodine, permits the transfer of electrons from one phthalocyanine ring to another. Electrons move between phthalocyanine rings separated by bridging fluorine atoms, which provide sufficient separation between the bulky phthalocyanine rings to permit bonding but do not separate the rings so much that the separation becomes a barrier to conduction. It is hypothesized that sublimation occurs through reversible breaking/formation of the coordinate covalent bridge fluorine bonds.

The coordinating metal is either aluminum or gallium. If the metal is aluminum the preferred range for x is 0.01 to 2.5. The most preferred range for combined thermal stability and conductivity for aluminum is when x is from 0.4 to about 2.5, the latter compositions being obtained by heat treatment of compositions of higher iodine content. For gallium, the preferred range is from 0.01 to 1.8.

The PcMF polymers can be prepared by mixing a phthalocyanine metal hydroxide hydrate with aqueous hydrogen fluoride, drying the mixture in a nonoxidizing atmosphere, and heating the dried material in a nonoxidizing atmosphere to a temperature from about 275° C. to about 350° C. Preferably the nonoxidizing atmosphere is vacuum. There are two preferred ways of preparing the iodinated polyphthalocyanines of the present invention. The polymer is iodinated by exposing the PcMF polymer to an iodine-containing non-oxygen atmosphere at a temperature from the vaporization temperature of iodine to about 150° C. The presence may range from the vapor pressure or pressure of iodine alone when no other constituent is present in the vapor phase, to a pressure of 1 atm or above when a non-oxidizing gas, for example nitrogen, is present in addition to iodine vapor.

Iodinated polyphthalocyanines can also be prepared by the method comprising the steps of dissolving iodine in n-heptane or other unreactive organic solvent such as carbon tetrachloride, 1,1 or 1,2 dichloroethane, methylene chloride toluene or tetrahydrofuran to produce concentrations from about 0.001 g/100 ml to complete, saturation admixing $(PcMF)_n$ to said iodine, continuing mixing until reaction is complete, and separating the product.

The temperature of the reaction may range from about 0° C. to about 150° C., and preferably from 20°–50° C. Any desired composition in the ranges cited above may be obtained by using iodine as a limiting reagent. Completion of reaction can be monitored by TGA.

The compositions prepared by either of the above methods can be made to display greater thermal stability through thermal treatment. The temperature range for this treatment is from ambient temperature up to 200° C., although care must be used in this thermal treatment at elevated temperatures, especially near 200° C., as prolonged thermolysis at or above this temperature will effect complete loss of iodine and regeneration of PcMF. Any pressure may be used up to 1 atm, although atmospheric pressure is preferred for economic reasons. Any dry nonreactive atmosphere such as vacuum or nitrogen may be used. The preferred temperature range is from 80°–160° C. and the preferred time for treatment is from 1–20 minutes, with less time being required at higher temperatures. For a given iodine content, the compositions obtained by heat treatment have the same conductivity (within experimental error) as the compositions obtained by two methods (vacuum, solvent) described above. However, thermal stability is enhanced through the removal of less stable iodine species from the material (especially $I_5^-$ according to Raman spectroscopy), leaving more thermally stable iodine species (especially $I_3^-$).

The following examples are given by way of illustration and are not meant to limit this disclosure and the claims in any manner.

EXAMPLE I

Preparation of $(PcAlF)_n$

Phthalocyanine aluminum hydroxide hydrate ($PcAlOH \cdot yH_2O$) was evaporated to dryness three times with concentrated aqueous hydrofluoric acid. Heating the dried fluoride to 300° C. in vacuum for four hours provided bulk quantities of the polymer. The analytical data are as follows: Calcd. for $C_{32}H_{16}N_8AlF$: C, 68.88; H, 2.89; N, 20.1; F, 3.40; Al, 4.83. Found: C, 65.7, 67.2; H, 2.90, 2.84; N, 19.2, 19.5; F, -, 3.96.

EXAMPLE II

Preparation of $(PcGaF)_n$

The process of Example I was repeated for $PcGaOH \cdot xH_2O$. The analytical data are as follows—Calcd. for $C_{32}H_{16}N_8GaF$: C, 63.9; H, 2.68; N, 18.7; Ga, 11.6; F, 3.16. Found: C, 65.3; H, 2.70; N, 18.5; G, 10.2; F, 3.33.

EXAMPLES III & IV

Sublimation of $(PcAlF)_n$ and $(PcGaF)_n$

The products of Examples I and II were sublimed at $10^{-3}$ Torr using a sublimation apparatus (Model No. 8022 by Ace Glass, Inc.) which was modified by replacing the lower portion of the sample-holder tube (50 mm) with quartz. The furnace temperature was monitored with a pyrometer (Model No. 20700 by Fischer Scientific Instruments, Inc.). The approximate furnace temperatures for sublimation were 510°–530° C. for aluminum and 470° to 490° C. for gallium. The cold finger was cooled with water, which boiled vigorously under the sublimation conditions. The analytical data found (see calculated data above) for $C_{32}H_{16}N_8AlF$ are: C, 68.7; H, 2.97; N, 20.0; F, 3.23; Al, 5.00 and for $C_{32}H_{16}N_8GaF$ are: C, 63.8; H, 2.80; N, 18.6; Ga, 11.4; and F, 3.04.

EXAMPLE V

Preparation of $[(PcAlF)(I)_x]_n$ using Iodine Vapor (Unsublimed PcMF)

A reaction vessel was constructed by fusing a short piece (5 cm) of 22 mm tubing sealed at one end to that arm of a right-angle 8 mm Teflon needle valve colinear with the bore. An 18/9 o-joint was sealed to the other arm of the valve. After weighing the empty vessel (without the Teflon plug), a tube of glassine paper was inserted through the valve until it was in close proximity to the bottom of the tube. Unsublimed $(PcAlF)_n$ (nominally 1 g) was then carefully transferred through the paper tube into the reaction vessel, the paper tube was removed, the vessel reweighed, and the Teflon plug inserted. The vessel was then attached to a small manifold which provided iodine vapor from a tube filled with iodine crystals. Once assembled, the apparatus was evacuated, the valve to the main vacuum system was closed and the system was allowed to equilibrate at ambient temperature. During the initial stage of iodine uptake a change in color occurred for $(PcAlF)_n$ from blue-violet to dark violet-black. Iodine uptake was monitored periodically by removing the vessel containing $[(PcAlF)(I)_x]_n$ and weighing it with no exposure to the atmosphere. After reaching constant weight (two weeks) the reaction vessel was transferred to a glove bag (nitrogen atmosphere) where approximately half of the product was removed from characterization. The vessel was reattached to the vacuum line and pumped on for a few minutes for removal of readily volatile iodine from the remaining product before analysis. Elemental analysis (%) of the product—Found: C, 38.2; H, 1.62; N, 11.1; F, 2.42; and I, 40.8. Iodine analysis by TGA 43%. Formula PcAlFI$_{3.3}$.

EXAMPLE VI

Preparation [(PcAlF)(I)$_y$]$_n$ using an iodine heptane slurry (Unsublimed PcAlF)

Unsublimed (PcAlF)$_n$ (0.75 g) was treated with a clear solution of 1.5 g iodine in 100 ml heptane. The flask was stopped with a septum and stirred magnetically. Iodine uptake was monitored by daily filtration and TGA. Virtually all iodine uptake occurred within the first 24 hours. When the product (PcAlFI$_{1.5}$) was pumped on at $10^{-3}$ Torr at ambient temperature, approximately $\frac{1}{3}$ of the iodine originally present was eliminated in vacuo, leaving the product (PcAlFI$_{1.0}$).

EXAMPLES VII & VIII

Preparation of [(PcAlF)(I)$_x$]$_n$ using an Iodine/1,2 Dichlorobenzene Slurry (Unsublimed PcAlF)

Two reactions were carried out with slurries of (PcAlF)$_n$ in iodine/1,2-dichlorobenzene, one at 65° C. (VII) and the other at 103° C. (VIII). (PcAlF)$_n$ (1.0 g) was weighed and transferred into a round bottom flask containing 50 ml of 1,2-dichlorobenzene and a magnetic stir bar. A reflux condenser with drying tube was attached and heating and stirring begun. The temperature was maintained constant for 50 h (103° C.) for one reaction and 6 days (65° C.) for the other. The reaction mixture was then cooled to room temperature and filtered. The filter cake was washed with copious amounts of heptane until the filtrate was a pale pink. The powdery, nearly black material on the frit, was allowed to air dry. (PcAlFI$_{0.65}$) was obtained from the reaction at 65° C., while (PcAlFI$_{0.76}$) was obtained from the reaction at 103° C.

EXAMPLE IX

Preparation of [(PcAlF)(I)$_x$]$_n$ utilizing a PCAlF/I$_2$/Heptane Slurry (Sublimed PcAlF)

The preparative procedure of Example VI was repeated with sublimed (PcAlF)$_n$. TGA showed that maximum iodine uptake occurred in less than 5 min. Repeated runs showed that the iodine content could be controlled at any desired level (x=0.01-3.4) by using iodine as a limiting reagent. A complete elemental analysis was obtained on one of these compositions. Found: Al, 2.92; C, 38.30; F, 2.61; H, 1.60; I. 43.22; and N, 11.13. These data corresponds to the formula: Al$_{1.08}$ C$_{31.9}$ F$_{1.37}$H$_{1.60}$I$_{3.40}$N$_{7.95}$, i.e., PcAlFI$_{3.4}$.

EXAMPLE X

Preparation of [(PcGaF)(I)$_x$] Utilizing a PcGaF/I$_2$/Heptane Slurry—(Sublimed PcGaF)

The method of Example VII was repeated with sublimed (PcGaF)$_n$. During the initial stage of iodine uptake, the color became a deeper violet. The uptake of iodine was slower for PcGaF than for PcAlF. Thus it took 24 hours to produce (PcGaFI$_{1.18}$)$_n$. A complete analysis of one polymer gave: C, 52.26; F, 2.54; Ga, 8.95; H, 2.28; I, 16.15; N, 15.07. Formula found: C$_{32.2}$ F$_{0.993}$ G$_{0.972}$ H$_{16.9}$ I$_{0.94}$ N$_{8.00}$, i.e., PcGaFI$_{0.94}$.

EXAMPLE XI

Preparation [(PcGaF)(I)$_x$]$_n$ Iodine Vapor, (Unsublimed PcGaF)

The method of Example V was repeated for unsublimed (PcGaF)$_n$. The violet color of (PcGaF)$_n$ became darker. Iodine uptake was monitored periodically by removing the vessel containing [(PcGaF)(I)$_8$]$_n$ and weighing it with no exposure to the atmosphere. Constant weight was reached in three weeks, and the composition PcGaFI$_{2.2}$ was produced.

EXAMPLE XII

A sample of PcAlFI$_{3.3}$ prepared by the method described in Example IX was heated at ambient pressure in a stream of dry nitrogen at 60° C. for 15 minutes to yield PcAlFI$_{2.7}$. Further heating at 120° C. for 15 minutes yielded PcAlFI$_{0.9}$. Compositions with successively lower iodine content were prepared by increasing heating temperature and/or increasing time. Conductivity studies showed expected values for the various compositions as a function of iodine content, e.g. PcAlFI$_{2.7}$, 4.5 (ohm cm)$^{-1}$, PcAlFI$_{0.9}$, 0.23 (ohm cm)$^{-1}$.

EXAMPLE XIII

Samples of PcAlFI$_x$ prepared according to Example XII were examined for conductivity and thermal stability. Thus PcAlFI$_{0.9}$ prepared according to Example XII was placed in an open glass container and heated in a dry nitrogen atmosphere at 100° C. No measurable change in the conductivity recorded at ambient temperature was observed (0.24±0.05 (ohm cm)$^{-1}$) over the course of 72 hours. No change in conductivity of this sample was observed after further heating this sample in ambient air at 100° C. Another sample prepared according to Example XII (PcAlFI$_{0.69}$) was heated in ambient air at 150° C. for 48 hours. No observable change in conductivity measured at room temperature occurred over the course of this period.

Measurements were made on the preceding compounds by several techniques. Thermogravimetric analysis, along with an independent weight uptake measurements and chemical analysis, was utilized to determine the iodine content. Raman spectroscopy was utilized to study the nature of the iodine-containing species.

Thermogravimetric analysis (TGA) data were obtained using a DuPont 990 thermal Analyzer and 951 TGA module with a quartz furnace tube and platinum sample boat. A nitrogen flow rate of 50 ml/min and programmed heating rates of 5° C., 10° C. or 20° C./min were employed. Scans were routinely made from room temperature to approximately 400° C. and occasionally to 900° C. Initial sample mass was nominally 10 mg. Iodine analysis can be obtained directly from the thermograms; compositions containing from 2 to 43% iodine were analyzed in this manner. To confirm the TGA determinations, iodine analysis on a number of compositions was obtained.

Conductivity measurements consisted of the linear four-probe technique and Van der Pauw measurement. Sample discs (13 mm diameter×ca. 1 mm were formed using an evacuable die and Carver Press. The brittleness of the discs necessitated careful handling. Disc thickness was determined with the aid of a microscope. Disc colors ranged from highly reflective magenta for pure (PcMF)$_n$ to dark maroon for highly iodine-doped compositions.

The linear four-probe technique measured room temperature d.c. conductivities and utilized an Alessi Industries (Costa Mesa, CA) unit (1 mm probe spacings) connected to a Keithley Instruments (Cleveland, Ohio) Model 530 Type-All system. A model 616 electrometer was substituted for the model 163 digital voltmeter. Resistivities were calculated as described by Valdes (Proc. I.R.E., 42, 420 (1954)).

Data accumulation and processing for the Van der Pauw measurements, with the exception of manual selection of sample-current input, were microprocessor controlled. Current to the sample was supplied by a Keithley Model 225 constant current source. Output d.c. voltages were detected by a Keithley Model 616 electrometer linked to a Tektronix 4051 computer via a Data Precision Model 3400 digital voltmeter and an IEEE 488 (1975) interface bus. Electrical contacts to the sample discs were made with either DuPont No. 4817 silver paint or with a dispersion of carbon black and cellulose caprate in ethyl acetate. The latter proved esential for the highly iodinated samples as the silver paint contacts resulted in undesirable battery voltages up to ±600 mv with zero applied current. To provide strain-free mounting, discs were secured to the anodized aluminum mount with a tuft of cotton over which was wrapped a strip of Teflon tape. The sample and holder were contained in a gas-tight brass can which fit into a liquid nitrogen dewar centered between the poles of an electromagnet (0-5 kG magnetic field) for Hall voltage measurements. Thermal coupling to the sample mount was aided by providing a helium atmosphere inside the can. A Eurotherm (Model 917) temperature controller (with computer-controlled set-point) regulated the power input to the heating coil wrapped around the aluminum mount. A type E (Chromel-Constantan) thermocouple located ca. 1 mm from the sample monitored sample temperature ($\mp 0.1°$ C.). The measurement procedure included (a) verification of electrical isolation between the sample and mount, (b) resistance measurements between all four electrodes as a function of current to check for non-ohmic behavior, contact resistance, and sample integrity, and (c) measurements at zero current to the sample to check for stray voltages. Room temperature measurements were performed first. Sample temperature was then dropped to 77 K (66 K in one case) and data collection between 77 K and room temperature begun. Reproducibility of the initial room temperature data verified sample stability over the temperature range studied. At temperatures much above ambient, highly iodinated, non-heat treated samples released iodine slowly and stable voltages could not be recorded. This instability limited variable temperature studies to temperatures near or below ambient.

Raman spectra were obtained with a Spex Ramalog 6 spectrometer employing 514.5 nm excitation (50 mW argon ion laser power). Sample discs were spun at 3000 rpm. Infrared spectra were recorded on samples contained in KBr discs with a Perkin-Elmer Model 267 spectrophotometer. Mass spectra were obtained with a Hewlett-Packard 5985 quadrupole instrument (70 eV ionizing electrons). The samples, in glass capillaries, were introduced into the spectrometer via the variable temperature (30° to 300° C.) solid probe inlet system. A heating rate of 20° C./min was employed. Both Fragmentation patterns and profiles of $I_2^+$ (m/e 254) intensity as a function of temperature were generated.

Tables I and II summarizes the resuls of the above testing.

TABLE I

| | (Al) | | |
|---|---|---|---|
| Ex. No. | I/Al | Conductivity (ohm cm)$^{-1}$ | Activation Energy eV |
| III | 0 | $10^{-7}$ | — |
| V | 3.3 | 0.59 | 0.03 |
| VI | 1.0 | 0.13 | 0.05 |
| VII | 0.65 | 0.20 | — |
| VIII | 0.76 | 0.24 | 0.05 |
| IX | 3.4 | 3.4 | — |
| XII | 2.7 | 4.5 | — |

TABLE II

| | (Ga) | | |
|---|---|---|---|
| Ex. No. | I/Ga | Conductivity (ohm cm)$^{-1}$ | Activation Energy eV |
| IV | 0 | $10^{-9}$ | 0.85 |
| X | 1.18 | 0.12 | — |
| XI | 2.1 | 0.15 | 0.04 |

The reaction of (PcMF)$_n$ with iodine produced highly conducting compositions as fine purple black powders for M=Al or magenta to purple-black powders for M=Ga. Due to the thermal and oxidative stability of the (PcMF)$_n$ substrate, the iodine content was readily determined by TGA.

The rate and extent of reaction of PcAlF and PcGaF is dependent on PcMF purity and reaction conditions. Sublimed PcAlF reacts with a saturated pentane/iodine solution to give [PcAlFI$_{3.3}$]$_n$, in less than 5 min while with unsublimed PcAlF a maximum I/Al ratio of 1.5 is obtained in 24 hours. The reaction of unsublimed PcAlF with iodine vapor proceeds slowly at ambient temperature, with [PcAlFI$_{3.4}$]$_n$ being obtained after 3 weeks. With sublimed PcGaF, PcGaFI$_{1.18}$ forms after 24 hours using iodine/pentane, while unsublimed PcGaF gives [PcGaF$_{0.98}$]$_n$ under similar conditions. Unsublimed PcGaF yields (PcGaFI$_{2.1}$)$_n$ on reaction with iodine vapor at ambient temperature.

(PcMFI$_x$)$_n$ compounds prepared as described in the previous paragraph are unstable in vacuo and slowly lose iodine over a period of days to weeks finally giving stable compositiions. Thus, (PcAlFI$_{3.4}$)$_n$, initially obtained from the solid-vapor reaction, loses iodine to form (PcAlFI$_{2.4}$)$_n$, after two weeks in vacuo. (PcAlFI$_{1.5}$)$_n$, obtained from the iodine/heptane slurry reaction, is also unstable. This composition changes to (PcAlF$_{1.0}$)$_n$, after exposure to dynamic vacuum for two weeks. Samples pumped to constant weight at ambient temperature evolved small quantities of iodine when stored at ambient temperature and pressure, as evidenced by the discoloration of the polyethylene caps of the storage vials.

As described in Example XIII, a thermal treatment of iodinated PcAlF compositions improved their thermal stability. Samples which were heated so as to remove iodine last at low temperatures (up to approximately 200° C.) for a short period of time (typically 10–15 minutes) showed much improved thermal stability (to 150° C. in air).

At elevated temperatures (ca. 250° C.) under dynamic vacuum complete removal of iodine is effected leaving (PcMF)$_n$ which was identified by elemental analysis and TGA.

Variable temperature mass spectral data were collected to confirm the nature of the volatile species. The fragmentation pattern for each sample showed a base peak at m/e 254 (I$_2^+$). Profiles of total ion current were nearly identical to the profiles of I$_2^+$ intensity vs temperature establishing iodine as the predominant volatile during thermolysis of (PcMFI$_x$)$_n$.

The room temperature pressed disc d. c. conductivities obtained by both the linear four-point probe and van der Pauw methods are in excellent accord for all samples. A linear four-probe conductivity value of $10^{-6}$ ohm$^{-1}$ cm$^{-1}$ was measured for sublimed (PcAlF)$_n$ and for (PcAlF)$_n$ regenerated by prolonged heating of (PcAlFI$_{2.4}$) to 200° in vacuum. Thus, striking increases in conductivity—as much as $10^{-9}$ for (PcGaF)$_n$—occur upon doping with iodine.

With (PcMFI$_x$)$_n$ the highest iodine dopant levels give higher conductivity for Al than for Ga. This observation correlates with the greater inter-phthalocyanine ring spacing for Ga vs. Al and provides evidence that the conductive pathway is through a conduction band generated by inter-ring pi-orbital overlap.

A portion of this work was first disclosed in Paul M. Kuznesof and Kenneth J. Wynne, *J.C.S. Chem. Comm.*, 121-2, 1980, which is hereby incorporated by reference.

In summary we have shown that iodine-doped (PcMF)$_n$ compositions are highly conducting. They have lower thermal stability with regard to loss of iodine compared to iodine doped (PcSiO)$_n$, but because the polymer chain is linked by coordinate covalent bonds in (PcMF)$_n$, these materials can be sublimed and doped to give conducting thin films. The conductivity of [(PcMF) (I)$_x$]$_n$ is equal to or greater than the SiO linked analogs. The improved conductivity of (PcMFI$_x$)$_n$ may be due in part to the capability of purification of (PcMF)$_n$ by sublimation vs. (PcSiO)$_n$ which is less tractable. The highest conductivity of [(PcMF)I$_x$]$_n$ is factor of 10 greater than the highest conductivity of [(PcM)(I)$_x$]$_n$ or [(PcMO)(I)$_x$]$_n$ polymers.

What is claimed as new and desired to be secured by Letters Patent of the United States is:

1. An iodine-doped polyfluorometallophthalocyanine having the repeating unit of (PcMF)(I)$_x$ wherein Pc represents a phthalocyanine moiety M represents a III-A metal selected from the class consisting of aluminum and gallium, and x is from about 0.01 to about 3.4 if M is aluminum and x is from about 0.01 to about 2.3 if M is gallium.

2. The polyfluorometallophthalocyanine of claim 1 wherein M represents aluminum.

3. The polyfluorometallophthalocyanine of claim 1 wherein M represents gallium.

4. The polyfluorometallophthalocyanine of claim 2 wherein x is from 0.4 to 2.5.

5. The polyfluoromethallophthalocyanine of claim 3 wherein x is from 0.4 to 1.5.

6. The polyfluorometallophthalocyanine of claim 1 wherein x is from 0.4 to 0.6.

* * * * *